United States Patent [19]

Frassica

[11] Patent Number: 5,217,440
[45] Date of Patent: Jun. 8, 1993

[54] MULTILAMINATE COILED FILM CATHETER CONSTRUCTION

[75] Inventor: James J. Frassica, Chelmsford, Mass.

[73] Assignee: C. R. Bard, Inc., Murray Hill, N.J.

[21] Appl. No.: 958,546

[22] Filed: Oct. 8, 1992

Related U.S. Application Data

[63] Continuation of Ser. No. 728,845, Jul. 9, 1991, abandoned, which is a continuation of Ser. No. 418,148, Oct. 6, 1989, abandoned.

[51] Int. Cl.⁵ ............................................. A61M 25/00
[52] U.S. Cl. ............................... 604/282; 493/303; 156/184; 156/87; 604/280
[58] Field of Search ............... 128/657, 658, 772; 604/264, 265, 280–282; 72/147, 148; 493/292, 299, 301, 303, 304; 264/319, 320, 322, 149, 150; 156/86, 184, 203, 215

[56] References Cited

U.S. PATENT DOCUMENTS

| | | |
|---|---|---|
| 3,131,615 | 5/1964 | Schur . |
| 3,416,531 | 12/1968 | Edwards . |
| 3,485,234 | 12/1969 | Stevens .................... 604/282 X |
| 3,498,286 | 3/1970 | Polanyi et al. ............ 204/282 X |
| 3,554,237 | 1/1971 | Pelley ........................ 138/122 |
| 3,598,126 | 8/1971 | Hoeltzenbein ............. 604/282 |
| 3,618,614 | 11/1971 | Flynn ....................... 604/282 X |
| 3,684,605 | 8/1972 | Zwart . |
| 3,861,972 | 1/1975 | Glover et al. .............. 156/86 |
| 3,879,516 | 4/1975 | Wolvek ..................... 264/135 |
| 3,924,632 | 12/1975 | Cook ......................... 128/348 |
| 4,080,999 | 3/1978 | Bulters et al. ............. 138/125 |
| 4,081,303 | 3/1978 | Rogers et al. ............. 156/192 |
| 4,133,972 | 1/1979 | Andersson et al. ........ 174/47 |
| 4,262,704 | 4/1981 | Grawey ..................... 138/130 |
| 4,400,228 | 8/1983 | Gentry ....................... 156/184 X |
| 4,411,655 | 10/1983 | Schreck ..................... 604/165 |
| 4,425,919 | 1/1984 | Alston, Jr. et al. ........ 128/658 |
| 4,430,083 | 2/1984 | Ganz et al. ................ 604/283 |
| 4,463,779 | 8/1984 | Wink et al. ................ 138/125 |
| 4,478,898 | 10/1984 | Kato ......................... 156/184 X |
| 4,510,974 | 4/1985 | Natori et al. .............. 138/137 |
| 4,547,193 | 10/1985 | Rydell ....................... 604/282 |
| 4,644,623 | 2/1987 | Raley et al. ............... 156/215 X |
| 4,647,326 | 3/1987 | Pott .......................... 156/77 |
| 4,655,769 | 4/1987 | Zachariades .............. 623/1 |
| 4,707,206 | 11/1987 | Trepus, Jr. et al. ........ 156/187 |
| 4,740,207 | 4/1988 | Kreamer .................... 623/1 |
| 4,777,955 | 10/1988 | Brayton et al. ........... 128/642 |
| 4,784,144 | 11/1988 | Ono et al. ................. 128/634 |
| 4,817,613 | 4/1989 | Jaraczewski et al. ..... 128/658 |
| 4,863,442 | 9/1989 | DeMello et al. .......... 604/282 |
| 4,892,099 | 1/1990 | Ohkawa et al. ........... 606/194 |
| 4,899,787 | 2/1990 | Ouchi et al. .............. 138/131 |
| 4,923,541 | 5/1980 | Burger ...................... 156/87 |
| 4,955,377 | 9/1990 | Lennox et al. ............ 128/401 |
| 4,969,890 | 11/1990 | Sugita et al. .............. 606/192 |
| 4,976,691 | 12/1990 | Sahota ....................... 604/96 |

*Primary Examiner*—John D. Yasko
*Assistant Examiner*—Adam J. Cermak
*Attorney, Agent, or Firm*—Wolf, Greenfield & Sacks

[57] ABSTRACT

A catheter shaft and catheter are formed by spirally rolling a thin polymeric film about a mandrel into a tubular form and fixing the spirally wound film in the tubular form. Additional elements and films may be incorporated into the spirally wound tube to provide a catheter having varied characteristics and functions.

42 Claims, 5 Drawing Sheets

MULTILAMINATE COILED FILM CATHETER CONSTRUCTION

This application is a continuation of application Ser. No. 07/728,845, filed Jul. 9, 1991, now abandoned, which is a continuation of application Ser. No. 07/418,148, filed Oct. 6, 1989, now abandoned.

FIELD OF THE INVENTION

This invention relates to catheters and to new methods for making catheters

BACKGROUND OF THE INVENTION

For many years, catheters have been for a wide variety of medical procedures. Numerous types and variations of catheters have been developed for medical procedures. Among the advantages of using a catheter is that it is inserted into the patient through a small opening, either natural or made by a puncture. Typically, the catheter is used to perform a function deep within the body. The catheter enables the region of the body to be treated with minimal invasion and trauma. Often the use of a special purpose catheter to treat a condition may reduce the need for surgery. The use of a catheter often avoids long recuperative periods typical of more general surgical treatment.

By way of illustration, a catheterization procedure known as percutaneous transluminal angioplasty (PTA) is used to enlarge the lumen in an artery narrowed by plaque by delivering a catheter having a balloon at its end to the stenosisin (the narrowing) in the patient's artery. The balloon, once manipulated into the stenosis, can be inflated to unblock the artery and reestablish good blood flow through the artery. The procedure takes a few hours and the patient may resume activities, often at an increased level, within a day or two. By contrast, surgical intervention to remedy obstructed coronary arteries (coronary artery bypass surgery) is an extensive procedure, taking many hours, requiring surgical access through the chest wall to the patient's heart, typically requiring a recuperative period of many months.

Numerous other uses of a wide variety of catheters may include angiography, urinary, wound or chest drainage, optical examination and diagnosis of numerous lumens and body cavities and the like.

Catheters typically are made from materials suited particularly for the specific purpose to which the catheter is to be put. For example, the materials may be selected to provide a desired degree of flexibility or stiffness to the catheter or to provide regions of varying flexibility and stiffness along the length of the catheter. Materials may be selected to facilitate the ability of the catheter to transmit torque from the proximal end to the distal end of the catheter. In other instances the catheter may be made from materials having selected electrically conductive or insulative properties. Often it is desirable to provide either the inner or outer surface, or both surfaces, of the catheter with desired surface characteristics, such as lubricity or anti-clotting properties. It may be desirable to provide a catheter having optical capability by which light may be transmitted between the proximal and distal ends of the catheter. It ma be desirable to attach one or more balloons to the catheter and to provide inflation/deflation lumens for inflation and deflation of the balloons(s) as well as to provide other lumens for other purposes. Additionally it is a frequent requirement that the catheter maintain as small an outer diameter as possible, a requirement that often requires compromises to be made in the construction of the catheter such as, for example, dimensional compromises in wall thickness, lumen size or the like.

Catheters frequently have multiple requirements or functions. For example, often it is desirable that part of the catheter be stiff while another part of the catheter be flexible. It is common for catheters to have portions that are electrically conductive alternated with portions that are insulative. Thus, catheters often have different constructions either in the materials, components or shape or the like at different locations along the catheter.

A typical catheter construction involves the extrusion of a selected polymeric material into a tubular catheter shaft having one or more lumens. A wide variety of polymeric materials are in common use such as polyvinyl chloride, polyethylene, polytetrafluoroethylene, urethane formulations, polyesters and the like. In a typical catheter construction other elements are added to the shaft such as balloons, fittings, connectors, coatings, transducers, optical fibers, conductors, electrodes, braids and the like. Numerous finishing operations typically are required in order to assemble the catheter. The manufacturing procedure is labor intensive. Other techniques for manufacturing a catheter shaft also include the molding as well as the repetitive coating of multiple layers built up on a mandrel. Often the manufacturing procedure imposes limitations on the nature and the number of characteristics that a particular catheter might incorporate.

As catheterization procedures have developed, there has been an increasing tendency to build catheters with thinner walls. By making the catheter with a thinner wall, the catheter is provided with increased internal space for additional lumens or the ability to increase the size of the existing lumen(s) without increasing the overall outer diameter of the catheter. It also may enable the outer diameter of the catheter to be reduced so that the catheter may be more easily advanced into the body lumen or internal body location to be treated. As the demands for higher performance, multiple function catheters has increased, it has become increasingly difficult to manufacture such thin wall, multi-function catheters utilizing existing catheter manufacturing techniques. Among the difficulties is that catheters having very thin walls may tend to kink when curved or bent, thus tending to close off the catheter lumens.

It is among the general objects of the invention to provide a new method for making catheters and a resulting new catheter construction which avoids many of the difficulties presented in prior catheter manufacturing techniques.

SUMMARY OF THE INVENTION

In accordance with the invention, an elongated tubular catheter is made by rolling an elongate thin film of material into a tube about a mandrel in a spirally coiled fashion. Other films or elements may be interposed in the spirally coiled film. The tube then is constricted about the mandrel to apply pressure to the tube and, while maintaining the constricting pressure, the layered tubular coiled film is bonded or fused together. The films may be formed from different materials to provide selected desired characteristics at desired locations on the catheter. The films may be specially shaped, contoured or etched to provide the desired characteristics when in the rolled configuration. Other elements may be incorporated into the spirally rolled film, such as optical fibers, hollow fibers, electrical conductors or the like, each adapted to provide the finished catheter with the desired properties and characteristics. A catheter so made achieves its objectives while incorporating a very thin wall construction.

It is among the general objects of the invention to provide a new catheter construction as well as a new technique and methods for manufacturing catheters.

Another object of the invention is to provide a catheter construction and method for manufacture of thin wall catheters.

A further object of the invention is to provide a new catheter construction and a new method for manufacturing such a catheter in which the catheter is provided with multiple and varied characteristics and properties.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
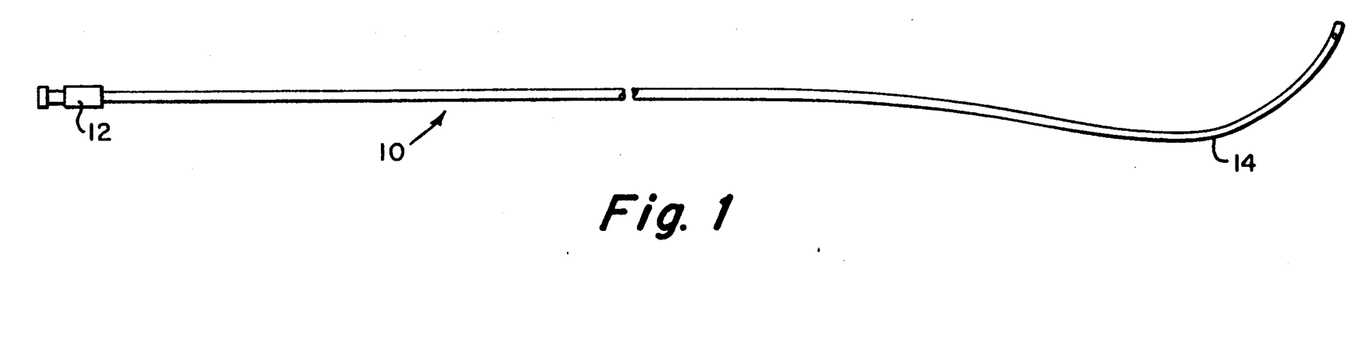
FIG. 1 is a fragmented illustration of an angiographic catheter.

FIG. 1 illustrates, generally, a catheter, such as an angiographic catheter for injecting radiographic contrast liquid into a blood vessel. The catheter includes an elongate tubular shaft 10 that has a lumen extending fully along its length. A fitting 12 is attached to the proximal end of the catheter for connection to a syringe or other device adapted to force radiographic contrast liquid through the lumen of the catheter. The distal end of the catheter terminates in an outlet from which the contrast liquid emerges. Angiographic catheters typically have a curved distal end, as suggested at 14, there being many different types of catheters having different curved configurations, each adapted for use in a specific procedure or for a particular technique. By way of further example, an angiographic catheter usually must be able to transmit torque from its proximal to its distal end so that the rotational position of the distal end can be manipulated and controlled from the proximal end in order that the outlet at the distal end of the catheter may be positioned in the blood vessel or other lumen precisely where desired. For example, in coronary angiography, it is essential that the outlet tip be located precisely and securely at the entrance to the coronary artery to be investigated. The burst strength of an angiographic catheter must be sufficient to withstand the substantial pressures that are developed during the injection of radiopaque contrast liquid. It is common for such catheters to have a pressure capability of the order of 1,000 psi. Such catheters also must have sufficient column strength so that they are "pushable" to facilitate advancement through and maneuvering in the arteries. The catheter should have the desired degree of stiffness but may be provided with a tip portion that is relatively soft and flexible.

Figure 1A:
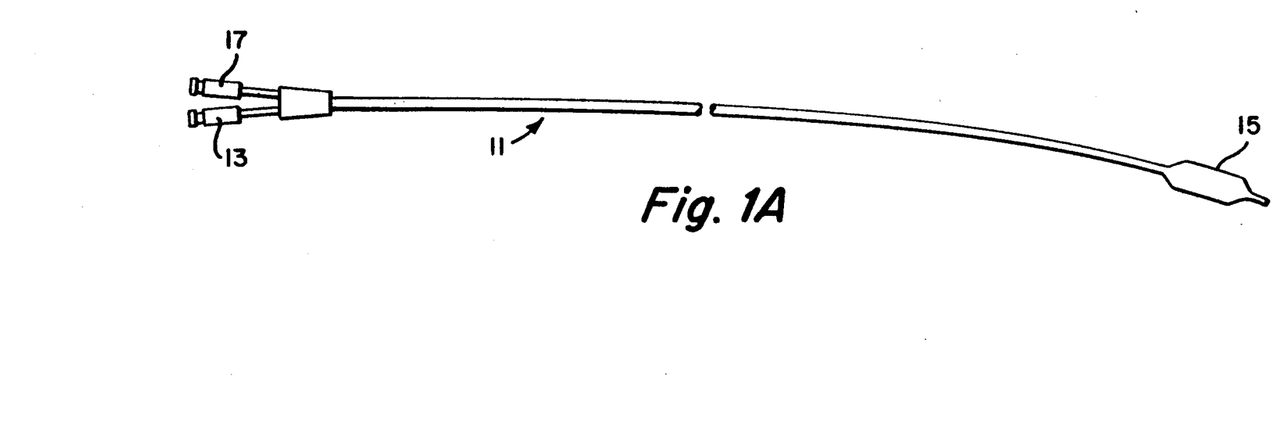
FIG. 1A is a fragmented illustration of a conventional balloon dilation catheter.

FIG. 1 A illustrates another conventional angiographic catheter, which incorporates the balloon for performing a distention procedure such as percutaneous transluminal angioplasty. As with the catheter shown in FIG. 1, the catheter illustrated in FIG. 1A includes an elongated tubular shaft 11, that has a lumen extending fully along it length. A fitting 12 is attached to the proximal end of the catheter for connection to a syringe or other device, which can force a fluid through the lumen of the catheter. The catheter is also provided with a second lumen, which connects a second fitting, 16, to a balloon structure 15, located on the distal end of the catheter. The balloon can be inflated and deflated in a conventional manner by means of fluid pressure applied to fitting 16.

Figure 2:
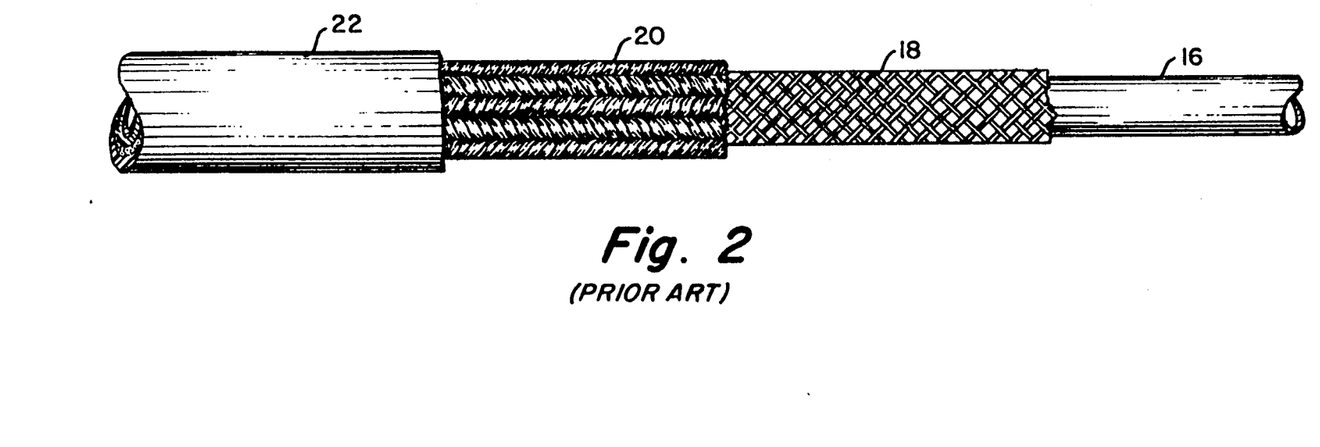
FIG. 2 is a fragmented illustration of a portion of the shaft of a finished angiographic catheter made in accordance with conventional prior art techniques.

FIG. 2 illustrates one of numerous types of construction presently embodied in an angiographic catheter. The catheter shaft includes an inner core 16 which may be made, for example, from a tube of extruded nylon. The inner core provides a core onto which the other layers of the catheter can be built. It contributes to the burst strength of the catheter and provides a relatively low friction surface to receive a guidewire. The inner nylon core 16 may be surrounded by a stainless steel wire braid 18 which enhances the torque transmission capability of the catheter as well as its burst strength. The wire braid 18 may terminate short of the distal tip of the catheter to enhance the softness at the distal tip. The wire braid 18 may be surrounded with an outer core 20 which may be woven from a relatively soft material such as Dacron. The woven outer core 20 enhances the torque characteristics of the catheter and also provides a matrix into which the outermost layer is embedded. The wire braid and Dacron layers typically are embedded and covered with a smooth, biocompatible polyurethane coating, indicated at 22. The polyurethane outer layer 22 may be formed by spraying or coating the built up catheter portions with the urethane material to build the urethane layer to the desired thickness. Different urethane compositions may be used at different portions of the catheter, for example, to vary the stiffness and softness characteristics at different locations on the catheter. By way of example, such a catheter may have a shaft with an outer diameter of the order of 0.104" (8F) and an inner lumen of the diameter of the order of 0.050". The fabrication of the catheter requires many procedural steps and is labor intensive.

Figure 3:
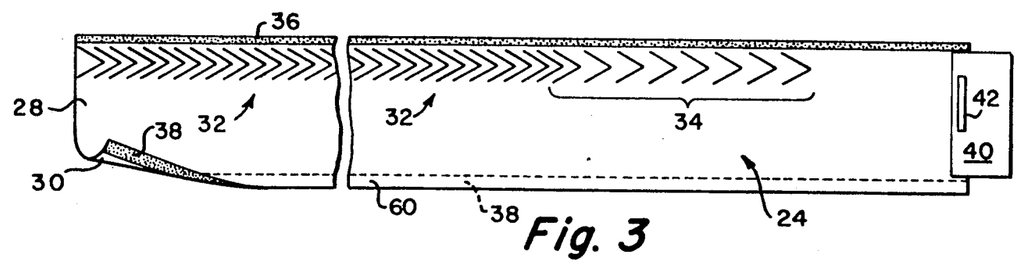
FIG. 3 is a plan illustration of a strip of flexible material from which a catheter may be made in accordance with the invention.
Figure 4:
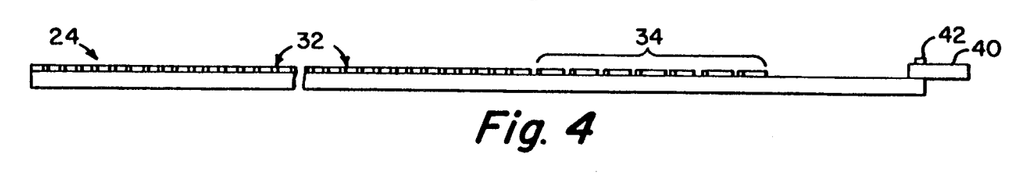
FIG. 4 is an edge view of the strip illustrated in FIG. 3 with the thicknesses of the various layers being highly exaggerated for purposes of illustration.
Figures 5, 6:
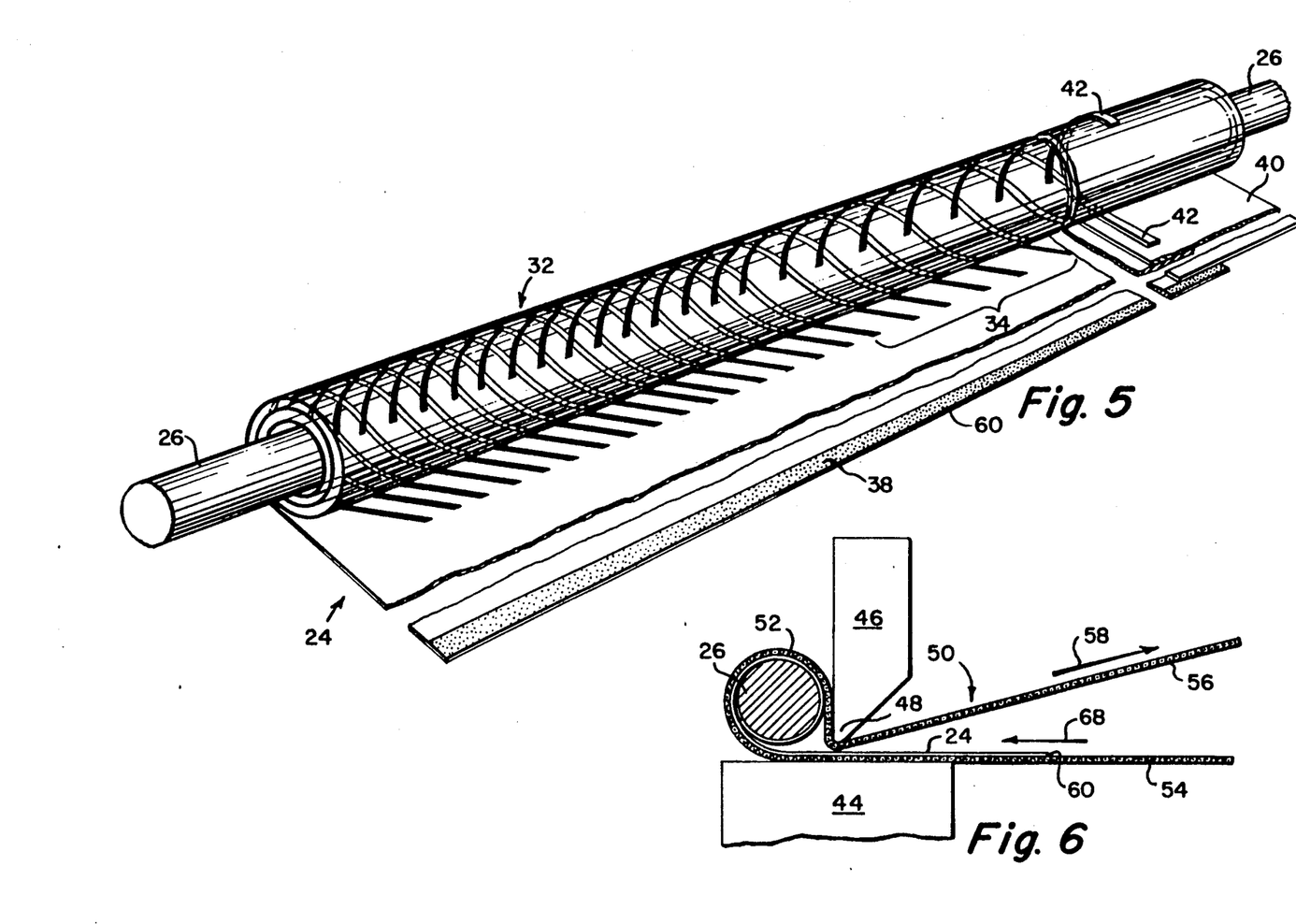
FIG. 5 is an illustration of the strip of FIGS. 3 and 4 being rolled into a tubular configuration.
FIG. 6 is an illustration of a device that may be used for wrapping the films onto a mandrel into the desired catheter configuration.
Figure 10:
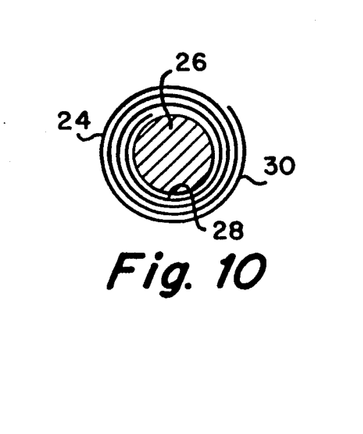
FIG. 10 is a cross-section of the helically-rolled tubular catheter shaft prior to constriction and bonding.

In accordance with the present invention, a catheter shaft is formed by providing an elongate strip of a thin film of material and by rolling that film onto a mandrel in a spiral, jelly roll-like fashion. FIG. 5 illustrates the manner in which such a catheter may be made, with FIGS. 3 and 4 illustrating an elongate thin film strip used in making the catheter. As shown in FIGS. 3 and 4, an elongate film strip 24, formed from an appropriate polymeric material is provided. For purposes of illustration only, the strip 24 may be formed from polyethylene. It may be of the order of 0.003" thick and may have a width of the order of 2.5". It may be approximately 125 cm long, corresponding to the intended length for the catheter. In accordance with the invention, a mandrel, indicated at 26, is provided and, as suggested in FIG. 5, the film strip 24 is wound spirally into a roll onto the mandrel 26. The film strip 24 may be considered as having an inner surface 28 and an outer surface 30, those designations corresponding to the direction in which the surfaces 28, 30 will face after the film strip 24 has been rolled into its tubular configuration. The completed spiral roll has the cross-sectional configuration shown in FIG. 10. After the film strip 24 has been wound onto the mandrel 29, the outer surface 30 faces towards the outside of the rolled strip, and the inner surface 28 faces towards the inside of the rolled strip.

The film strip 24 illustrated in FIGS. 3 and 4 is intended to form a tube having enhanced torsional rigidity in order that the resulting catheter can be torsionally manipulated. In prior catheters this has been achieved by including a tubular double helical sheath in the wall of the catheter as suggested at 18 in FIG. 2. In the present invention, the film strip is formed to define a double helical braid-like pattern when the film strip is rolled up. To that end, a pattern, formed from thin foil elements of the order of 0.001" thick may be applied to a surface, such as the inner surface 28 of the film strip 24. In the illustrative embodiment, the pattern may take the form of a plurality of chevrons extending along a substantial portion of the length of the film strip 24 from the proximal end (to the left in FIG. 3) toward the distal end (to the right in FIG. 3) of the film strip. The chevrons may be regularly spaced for most of the length of the film strip except that a distal group of chevrons 34 may be more widely spaced. The more closely spaced chevrons will result in a catheter region having somewhat greater torsional stiffness than in the more widely spaced chevron region 34. The chevrons, or other appropriate pattern, as desired, may be placed on the surface of the film strip 24 by any appropriate means, for example, by laminating a metal foil to the film strip 24 and then photochemically etching the unwanted portions to result in the pattern of chevrons. In the illustrative embodiment, the chevrons are dimensioned and arranged so that they will form a braid-like pattern when the film strip 24 is wrapped onto a 0.067" diameter mandrel.

The pattern 32 of chevrons preferably is disposed inwardly from one longitudinal edge of the film strip 24 to leave a margin 36 which, when wrapped about the mandrel will define the inner surface of the lumen of the rolled up tube. The margin 36 thus may be coated with an appropriate material, if desired, to provide certain surface characteristics to the inner lumen of the tube. For example, it may be desirable to maintain a low friction surface on the inner lumen of the tube to minimize friction with a guidewire over which the catheter will be placed. For that purpose, the margin 36 may be coated with a material such as polytetrafluorethylene (Teflon). The width of the margin 36 is substantially equal to the inner circumference of the lumen to be formed. If it is desired to provide the outer surface of the catheter with a particular coating, that may be accomplished by forming the coating along the longitudinally extending margin 38 on the outer surface 30 of the film strip 24. The width of the marginal coating 38 should correspond to the outer circumference of the rolled up tube. By way of example, the marginal portion 38 may be coated with a thromboresistant coating to provide an anti-clotting characteristic for the outer surface of the catheter.

It may be desirable to provide the distal end of the catheter with a relatively soft tip. For that purpose, a short strip 40 may be attached to the distal end of the film strip 24, as by an appropriate adhesive, by heat bonding or other suitable means. The short soft tip portion 40 will be formed from a softer polymeric material than the film strip. For example, it may be formed from a softer polyethylene than that of the film strip 24. By way of example, the short soft tip may be of the order of 0.003" thick and about 2" wide, extending approximately 2 mm from the distal end of the film strip 24. When the composite strips are rolled onto the mandrel, the soft tip strip portion 40 will form a soft tip segment.

Should it be desired to incorporate a radiopaque marker in the distal end of the catheter, that may be achieved by attaching a thin strip of radiopaque material, such as a thin strip of gold. The gold strip may be of the order of 0.3" long, 1.0 mm wide and approximately 0.002" thick. When the composite film is rolled up onto the mandrel, the radiopaque marker strip 42 will form a radiopaque marker band.

FIG. 6 illustrates, in diagrammatic cross-section one manner of wrapping the elongate composite strip about the mandrel 26. The arrangement involves the use of an apparatus having a table or platform 44 and an overhead restraining bar 46. The lower end of the restraining bar 46 is tapered, as indicated at 48 and is spaced slightly from the surface of the platform 44. A belt 50, which may be endless, passes through the slot between the restraining bar 46 and platform 44 to form a loop 52 on one side of the restraining bar 46. The portions of the belt 50 on the other side of the restraining bar 46 may be considered as having a feeding segment 54 and a return segment 56. The belt 50 is driven in the direction indicated by the arrows 58. The device is used to roll the film strip 24 into the desired tubular configuration by placing the film strip 24 on the feeding segment 54 of the belt 50. The mandrel 26 is disposed within the loop segment 52 of the belt 50. Both the feeding segment 54 and return segment 56 of the belt 50 are tensioned to draw the loop 52 snugly about the mandrel 26 and, in that configuration, the belt 50 is advanced in the direction indicated by the arrows 58. Thus, the feeding segment 54 of the belt 50 will carry the film strip 24 into the loop 52 while simultaneously rotating the mandrel 26. The leading longitudinally extending edge of the film strip 24 will be gripped between the loop 52 and the mandrel 26. Continued advancement of the belt 50 will continually draw the film strip 24 into the loop 52 and about the mandrel 26 to wrap into a spiral configuration about the mandrel 26. It may be desirable to provide the trailing margin 60 on the inner surface 28 of the film 24 with adhesive so that when the rolled up tube, mounted on the mandrel 26, is removed from the loop 52, it will remain in its spirally wound configuration on the mandrel 26, in readiness for the next step in the manufacturing process.

Figures 7, 8:
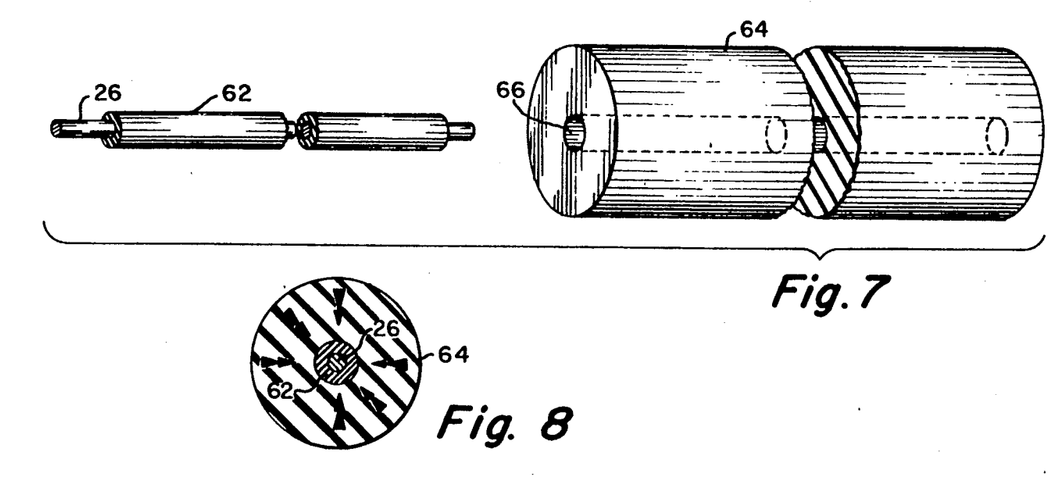
FIG. 7 is an illustration of further processing of the helically rolled tubular catheter shaft by which the helically rolled tube may be constricted and bonded in order to complete the catheter shaft.
FIG. 8 is a sectional view taken through the arrangement of FIG. 6 illustrating a constricting force being applied to the rolled up catheter shaft.

FIG. 7 illustrates, diagrammatically, the next step in the manufacturing procedure, in which the rolled up tube, indicated at 62, mounted on the mandrel 26 is subjected to a constricting force while applying heat to fuse the spiral layers of the tube together or by adhesively attaching the spiral layers together. In the later case, a thin film of appropriate adhesive may be applied over some or all of the surface of the film strip 24.

In order to apply the constricting force, the spirally rolled up film 62, mounted on the mandrel 26, is inserted into an elongate constrictible tube, indicated generally at 64. The constriction tube 64 has a central lumen 66 intended to receive the assembly of the tube 62 and mandrel 26. The constriction tube 64 may be formed from silicone rubber tubing which, after the assembled tube 62 and mandrel 26 are inserted into the lumen 66, may be caused to constrict tightly about the assembly and heated. More specifically, the lumen 66 of the silicone rubber tubing has an inner diameter that is slightly smaller than the outer diameter of the rolled up tube 62 on the mandrel 26. The silicone constriction tubing 64 may be caused to expand by soaking it in 1,1,2trichloro-1,1,1trifluoro-ethane (Freon). When in its expanded configuration, the assembly of the tube 62 and mandrel 26 is inserted into the lumen 26. The Freon then is allowed to evaporate which causes the tube 64 to shrink to its original configuration thereby exerting constricting pressure on the roll. The assembly then may be heated in a glycerine bath, for example, at 130° C. to fuse the layers of the roll into an integral walled catheter. After approximately 15 minutes, the assembly may be removed from the glycerine bath and cooled in a room temperature water bath for approximately 2 minutes. The silicone rubber tubing then may be stripped off to reveal the final shaft having an integral wall.

Figure 9A:
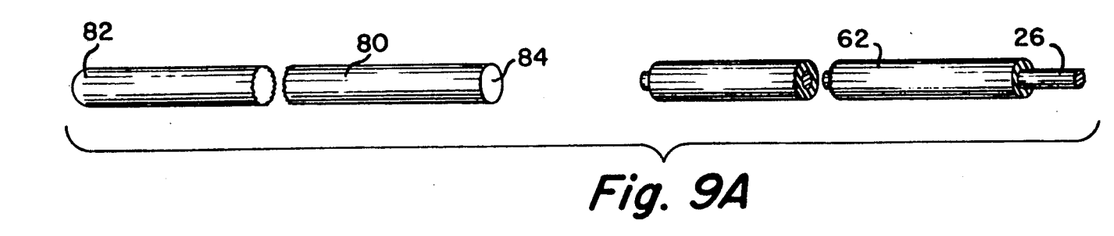
FIG. 9A is a schematic illustration of a portion of an alternative process for constricting and bonding the helically-rolled tubular catheter shaft.
Figure 9B:
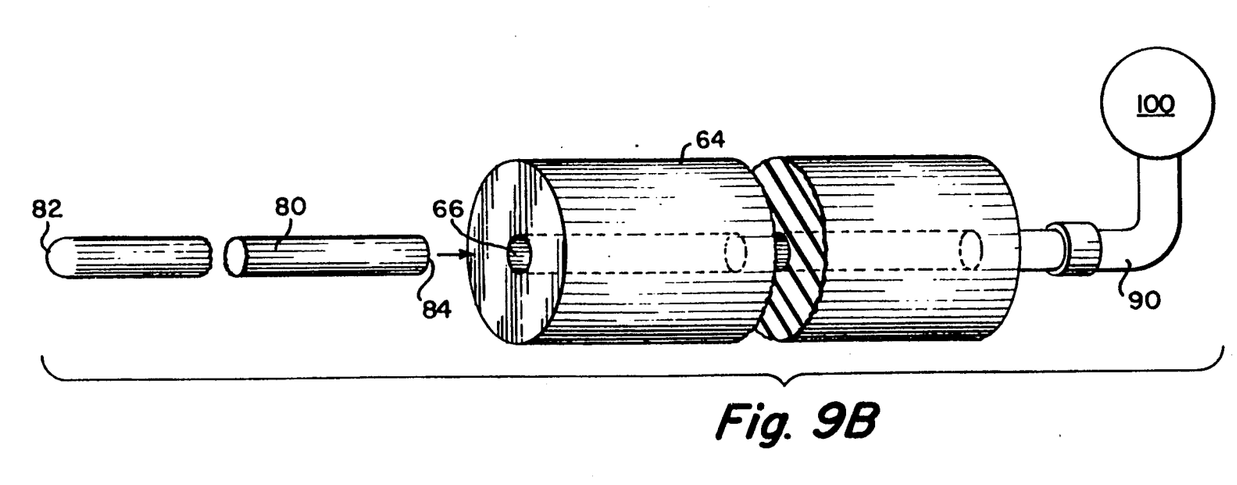
FIG. 9B is an illustration of further steps in the process of FIG. 9A for finishing construction of the helically-rolled tubular catheter shaft.

In another technique for inserting the assembly of the roll 62 and mandrel 26 into the silicone rubber tube illustrated in FIGS. 9A and 9B, an elongate stainless steel tube 80, having one end sealed 82 and the other end opened 84 is provided. The assembly of the tube 62 and mandrel 26 is inserted into the open end 84 of the tube 80. The open end 84 of the tube 80 then is inserted into one end of the silicone rubber tubing. The other end of the silicone rubber tubing is attached to a source of pressurized air 100, by means of hose 90. As the air pressure in the silicone rubber tubing builds, it causes it to expand and form a cushion of pressurized air separating the inner surface of the silicone rubber tube and the outer surface of the stainless steel tube 80. In that configuration, the stainless steel tube 80, carrying the assembly of the tube 62 and mandrel 26, can be inserted into the silicone rubber tubing. Once the stainless steel tube 80 has been fully inserted, thus carrying the assembly of roll 62 and mandrel 26 fully into the silicone rubber tubing, the stainless steel tubing 80 may be withdrawn while maintaining the cushion of air under pressure. When the stainless steel tubing 80 is withdrawn, it leaves the tube 62 and mandrel 26 within the silicone rubber tubing until the air pressure is released which enables the silicone rubber tubing to constrict about the tube 62 and mandrel 26. The assembly then may be heated as described above to cause the layers to fuse together in the heated bath. The silicone rubber tubing and mandrel 26 then may be removed, leaving the composite catheter shaft. Alternately, it may be possible to insert the assembly of the roll 62 and the mandrel 26 into the silicone rubber tube without first placing it into the elongate stainless steel tube. This simplified technique would be preferable.

The catheter shaft may be finished as desired, such as by forming an appropriate curve in the distal end, by forming a taper in the distal portion, by adding a fitting to the proximal end of the catheter and the like. If desired, additional coatings may be formed on the catheter so made, as by spraying or otherwise coating.

Figure 11:
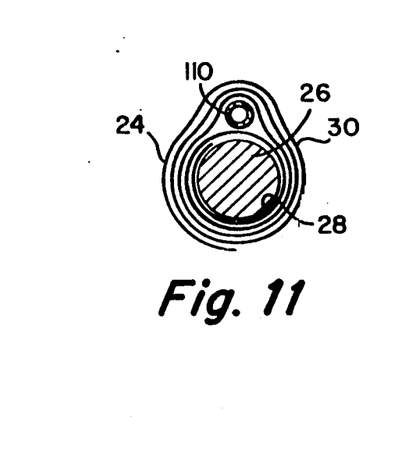
FIG. 11 is a cross-section of a helically-rolled tubular catheter shaft shown prior to constriction and bonding and which incorporates a second lumen.

A wide variety of catheters may be formed using the foregoing technique. For example, catheters may be formed to include elongate small diameter tubes that may be laid in with the film strip, so as to define one or more lumens in the wall of the catheter. Such a construction is shown in cross-section in FIG. 11 and consists of the spirally wound film strip 24, which incorporates a small diameter lumen 110 within the spirally formed wall. Such lumens may serve as inflation lumens, or may carry optical fibers or the like. Similarly, optical fibers may be laid in with the spirally rolled film to provide a means by which light may be transmitted from the proximal to the distal end of the catheter. Fibrous materials, such as fiberglass strands may be laid in with the roll for additional strength or other characteristics if desired.

Thus, it should be understood that the foregoing description of the invention is intended merely to be illustrative thereof and that other embodiments modifications and equivalents may be apparent to those skilled in the art without departing from the spirit of the invention. Having thus described the invention, it is my intention to claim and secure by Letters Patent the invention as defined in the following claims and equivalents thereof.

I claim:

1. A catheter for insertion into the human body comprising:
    an elongate tubular shaft formed from at least one film of material rolled into an elongate tube having a plurality of layers and permanently fixed in said rolled configuration;
    said shaft being formed from a biocompatible material and having a proximal end and a distal end, the shaft being constructed to enable the distal end to be inserted into the body of a human patient;
    a fitting attached to the proximal end of the shaft;
    said catheter including means at the distal end of the shaft for treating a medical condition of the patient, the catheter being manipulable from the proximal portion thereof disposed outside of the patient's body.

2. A catheter as defined in claim 1 further comprising at least one additional element formed from a different material and incorporated into the wall of the elongate tube.

3. A catheter as defined in claim 2 wherein the film is formed from a polymeric material.

4. A catheter as defined in claim 2 wherein the film is a polymeric film and the additional element comprises a hollow tubular member.

5. A catheter as defined in claim 2 wherein the film is polymeric and the additional element is elastomeric.

6. A catheter as defined in claim 2 wherein the first film is polymeric and the additional element is substantially radiopaque.

7. A catheter as defined in claim 2 wherein the first film is polymeric and the additional element is a low friction material.

8. A catheter as defined in claim 2 wherein the film is polymeric and the additional element comprises an electrical conductor.

9. A catheter as defined in claim 2 wherein said at least one additional element includes a film of different material disposed along a surface of said first mentioned film and defining the inner surface of the spirally rolled.

10. A catheter as defined in either of claims 2 or 9 wherein said at least one element includes a film of different material disposed along a surface of said first mentioned film and defining the outer surface of the spirally rolled material.

11. A catheter as defined in claim 1 wherein said means for treating or diagnosing a medical condition of the patient comprises a balloon carried on the catheter shaft and means for inflating and deflating the balloon while it is in the patient's body.

12. A catheter as defined in claim 1 wherein said means for treating or diagnosing a medical condition of the patient comprises optical means for transmitting light lengthwise of the catheter.

13. A catheter as defined in claim 1 wherein said means for treating or diagnosing a medical condition of the patient comprises electrically conductive means.

14. A catheter as defined in claim 1 wherein said means for treating or diagnosing a medical condition of the patient comprises a lumen for fluid communication between the interior and exterior of the patient's body.

15. A catheter as defined in claim 1 wherein said means for treating or diagnosing a medical condition of the patient comprises a transducer.

16. A catheter as defined in claim 1 wherein said means for treating or diagnosing a medical condition of the patient comprises electrodes.

17. A catheter as defined in claim 1 wherein said means for treating or diagnosing a medical condition of the patient comprises the distal end of the catheter having a predetermined curve formed therein adapted to facilitate a specific medical procedure.

18. A catheter as defined in claim 1 wherein said means for treating or diagnosing a medical condition of the patient comprises a fitting at the proximal end of the shaft.

19. A catheter as defined in claim 1 wherein said medical condition comprises a wound and the catheter includes means to drain the wound.

20. A catheter as defined in claim 1 wherein the catheter shaft is constructed and arranged to have sufficient torsional rigidity to enable torque to be transmitted from the proximal to the distal end thereby to facilitate navigation of the distal end of the catheter through the patient.

21. A catheter as defined in claim 1 wherein the shaft is constructed to have sufficient column strength so that it can be pushed through a lumen in the patient.

22. A catheter for insertion into the body of a human patient comprising:
an elongate tubular shaft formed from at least one film of material rolled into an elongate tube having a plurality of layers and permanently fixed in said rolled configuration;
said shaft being constructed to be inserted partly into the body of a patient;
said catheter including means for treating a medical condition of the patient, the catheter being manipulable from the portion thereof disposed outside of the patient's body;
at least one additional element formed from a different material and incorporated into the wall of the elongate tubular shaft, at least one of said additional elements extending over only a portion of the length of the tube.

23. A catheter as defined in claim 22 wherein the film is formed from a polymeric material.

24. A catheter as defined in claim 22 wherein the film is a polymeric material and the additional element comprises a metallic film.

25. A catheter as defined in claim 22 wherein the film is polymeric and the additional element comprises a hollow tubular member.

26. A catheter as defined in clam 22 wherein the film is polymeric and the additional element is fibrous.

27. A catheter as defined in claim 22 wherein the film is polymeric and the additional element is elastomeric.

28. A catheter as defined in claim 22 wherein the first film is polymeric and the additional element is substantially radiopaque.

29. A catheter as defined in claim 22 wherein the first film is polymeric and the additional element is a low friction material.

30. A catheter as defined in claim 22 wherein the first film is polymeric and the additional element is an optical fiber.

31. A catheter as defined in claim 22 wherein the first film is polymeric and the additional element comprises an electrical conductor.

32. A catheter for insertion into the body of a human patient comprising:
an elongate tubular shaft formed from at least one film of polymeric material rolled into an elongate tube having a plurality of layers and permanently fixed in said rolled configuration;
said shaft being constructed to be inserted partly into the body of a patient;
said catheter including means for treating a medical condition of the patient, the catheter being manipulable from the portion thereof disposed outside of the patient's body;
at least one additional element formed from a metallic film and incorporated into the wall of the elongate tubular shaft, at least one of said additional elements extending over only a portion of the length of the tube.

33. A catheter as defined in claim 32 wherein the metallic film is formed in a predetermined pattern.

34. A catheter as defined in claim 33 wherein the pattern forms a different pattern when rolled into tubular form.

35. A catheter having a shaft comprising:
at least one film of polymeric material spirally rolled into an elongate tube and permanently fixed in said rolled configuration; and
at least one additional element formed from a metallic film in a predetermined pattern comprising a plurality of chevrons and incorporated into the wall of the elongate tube, the pattern forming a different double helical pattern when rolled into tubular form.

36. A catheter for insertion into the body of a human patient comprising:
an elongate tubular shaft formed from at least one film of polymeric material rolled into an elongate tube having a plurality of layers and permanently fixed in said rolled configuration;
said shaft being constructed to be inserted partly into the body of a patient;
said catheter including means for treating a medical condition of the patient, the catheter being manipulable from the portion thereof disposed outside of the patient'body;
at least one additional element formed from a fibrous material and incorporated into the wall of the elongate tubular shaft, at least one of said additional elements extending over only a portion of the length of the tube.

37. A catheter for insertion into the body of a human patient comprising:
an elongate tubular shaft formed from at least one film of polymeric material rolled into an elongate tube having a plurality of layers and permanently fixed in said rolled configuration;
said shaft being constructed to be inserted partly into the body of a patient;
said catheter including means for treating a medical condition of the patient, the catheter being manipulable from the portion thereof disposed outside of the patient's body;
at least one additional element comprising an optical fiber and incorporated into the wall of the elongate tubular shaft.

38. A catheter for insertion into the body of a human patient comprising:
an elongate tubular shaft formed from at least one film of material rolled into an elongate tube having a plurality of layers and permanently fixed in said rolled configuration;
said shaft being constructed to be inserted partly into the body of a patient;
said catheter including means defining at least one lumen extending through the wall of the catheter shaft;
said catheter including means for treating a medical condition of the patient comprising a balloon at the distal end of the shaft in communication with the lumen,
the catheter being manipulable from the portion thereof disposed outside of the patient's body.

39. A catheter as defined in claim 38 wherein the lumen comprises a hollow elongate member contained within the catheter wall.

40. A catheter shaft as defined in any of claims 3-5 wherein the rolled tube is permanently fixed by fusing at least a portion of the polymeric film from which the catheter is rolled.

41. A catheter as defined in any of claims 1-39 wherein the shaft is permanently fixed by adhesive means bonding at least portions of the spirally rolled material.

42. A catheter shaft as defined in any of claims 6-31 wherein the rolled tube is permanently fixed by fusing at least a portion of the polymeric film from which the catheter is rolled.

* * * * *